United States Patent [19]

Denz et al.

[11] Patent Number: 5,298,865
[45] Date of Patent: Mar. 29, 1994

[54] CONNECTING CIRCUIT FOR CONNECTING A LAMBDA PROBE TO A CONTROL APPARATUS OF AN INTERNAL COMBUSTION ENGINE AND TEST METHOD FOR SAID CIRCUIT

[75] Inventors: Helmut Denz, Stuttgart; Werner Mezger, Eberstadt; Johannes-Dieter Wichterich, Hemmingen; Ernst Wild, Oberriexingen; Joachim Heimes, Eberdingen; Eugen Joos, Freiberg; Lothar Raff, Remseck; Eberhard Schnaibel, Hemmingen, all of Fed. Rep. of Germany

[73] Assignee: Robert Bosch GmbH, Stuttgart, Fed. Rep. of Germany

[21] Appl. No.: 872,810

[22] Filed: Apr. 24, 1992

[30] Foreign Application Priority Data

Apr. 24, 1991 [DE] Fed. Rep. of Germany ....... 4113316

[51] Int. Cl.[5] .......................... G01R 31/02; F01N 3/00; F02M 7/00
[52] U.S. Cl. ..................................... 324/509; 324/522; 340/649; 123/694; 60/274

[58] Field of Search .............. 324/399, 500, 509, 522, 324/555, 72, 72.5; 123/672, 676, 688, 690, 694; 60/274; 73/118.1; 340/649, 650

[56] References Cited

U.S. PATENT DOCUMENTS

| | | | |
|---|---|---|---|
| 4,526,147 | 7/1985 | Gnob | 123/694 |
| 4,622,809 | 11/1986 | Abthoff et al. | 60/274 |
| 4,951,632 | 8/1990 | Yakuwa et al. | 123/688 |
| 5,091,698 | 2/1992 | Grabs | 123/688 X |

Primary Examiner—Gerard R. Strecker
Assistant Examiner—Diep Do
Attorney, Agent, or Firm—Walter Ottesen

[57] ABSTRACT

The invention is directed to a connecting circuit for a potential-free lambda probe having a ground line and a signal line and having an offset voltage source which is connected to the ground line. This offset voltage source raises the potential of the ground line to a pregiven value relative to ground. A ground short is directly detectable in the connecting circuit of the invention in that the potential measured at the signal line drops below the offset voltage. In this way, it is no longer required as in conventional circuits to check for a ground short by enriching the mixture of an engine and to monitor the exhaust gas with the lambda probe.

6 Claims, 2 Drawing Sheets

CONNECTING CIRCUIT FOR CONNECTING A LAMBDA PROBE TO A CONTROL APPARATUS OF AN INTERNAL COMBUSTION ENGINE AND TEST METHOD FOR SAID CIRCUIT

FIELD OF THE INVENTION

The invention relates to a connecting circuit for a potential-free lambda probe having a ground line and a signal line as well as a test method for checking for faults when connecting the lambda probe such as short circuits or interruptions in the ground line or signal line.

BACKGROUND OF THE INVENTION

Lambda probes of the Nernst type have been known since the start of catalyzer technology with lambda control in motor vehicles and will be used most often also in the next few years. These lambda probes have a very steep characteristic; that is, the probe voltage changes only slightly with increasing rich mixture in the case of the measurement of a rich mixture and changes only slightly with lean mixtures with increasing lean mixture. However, in contrast, in the transition from a rich to a lean mixture within a very tight mixture range, a change of several 100 mV occurs. Typically, the probe voltage is at approximately 850 mV when measuring a rich mixture and at approximately 100 mV when measuring a lean mixture. The actual measured voltages fluctuate considerably however from one probe to another. A first probe can display 1 V when measuring a rich mixture and another probe can measure up to approximately −80 mV when measuring a lean mixture.

The above-mentioned characteristics specific to probes are quite insignificant for the control since with these probes typically only the inquiry is made as to whether the probe voltage lies above or below 450 mV. The characteristics specific to the probe lead however to problems when checking the connecting circuit as to faults especially if a short circuit to ground is present. 0 V is measured for short circuits to ground. This however is also a plausible measurement value since, as mentioned in the above paragraph, the voltage measured during lean can be 0 V or even lie therebelow with negative voltages not being evaluated by the typical evaluation circuits; that is, the negative voltages also lead to a measured voltage of 0 V.

In order to reliably determine short circuits to ground, the conventional practice is that when the probe voltage has a value of 0 V over a longer time span, the fuel/air mixture is arbitrarily enriched. If the probe signal does not respond to this enrichment, this is a reliable indication that a ground short is present. It is disadvantageous in this test method that the mixture must be enriched which leads to an increased exhaust of toxic gas and also causes other disadvantages.

Lambda probes are mostly so mounted that they detect the gas composition in the exhaust gas flow forward of a catalyzer. However, it is known for example from U.S. Pat. No. 4,622,809 that, in addition, a lambda probe can be mounted rearwardly of the catalyzer and, with the aid of this probe, the conversion capacity of the catalyzer is monitored. As long as the catalyzer converts well, a gas mixture of very uniform composition flows past the rearward lambda probe. For an engine controlled to the lambda value one, a voltage of approximately 450 mV is measured notwithstanding the relatively steep characteristic of the probe, since the lambda value rearward of the catalyzer is quite constant at the value one. This fact leads to difficulties when checking the operability of the probe rearward of the catalyzer since, for a probe voltage which is continuously uniform, it is unclear whether the connecting circuit for the rearward probe is defective or if the catalyzer converts so well that there are no changes. A check is possible also in this case in that over a longer period of time, a mixture is generated deviating from the lambda value one. This leads to the disadvantages already mentioned above.

SUMMARY OF THE INVENTION

In view of the above, it is an object of the invention to provide possibilities for checking the operability of the connecting circuits for lambda probes which operate without arbitrary change of the mixture composition.

The connecting circuit according to the invention is for a potential-free lambda probe having a ground line and a signal line. The connecting circuit includes an offset voltage source which is connected to the ground line in order to raise the potential thereof to a pregiven value with respect to ground.

When using such a connecting circuit, the lowest measured potential of the signal line can never have a lower value with respect to ground (when the circuit is operable) than that value which corresponds essentially to the offset voltage. In contrast, if the above-mentioned potential drops significantly below the offset voltage, it is certain that a ground short is present. The above-mentioned fault is noted directly when it occurs without a previous enrichment; that is, not only after a greater time span as with conventional methods.

The method according to the invention is for testing the connecting circuit of a potential-free lambda probe having a ground line and a signal line. The method includes the steps of: raising the potential of the ground line by a pregiven offset voltage with respect to ground potential; measuring the signal-line potential of the signal line relative to ground to determine if said signal-line potential is below a threshold value with said threshold value being at most equal to the difference between said offset voltage and the maximum possible amplified negative probe voltage; and, after determining that said signal-line potential is below said threshold value, then emitting a fault signal.

Not only ground shorts but also, for example, interruptions can be determined with the aid of the offset voltage. In order to also determine interruptions, it is advantageous to connect the signal line via a pull-down resistor to ground. This advantage applies especially for the connecting circuit of a probe mounted rearward of a catalyzer. For a probe mounted forward of a catalyzer, an interruption can be determined in the conventional manner in that the probe voltage remains continuously at a pregiven value.

BRIEF DESCRIPTION OF THE DRAWINGS

The invention will now be described with reference to the drawings wherein.

DESCRIPTION OF THE PREFERRED EMBODIMENTS OF THE INVENTION

In the following, resistors and voltage sources are often discussed. The designations of these components correspond to the resistance values and voltage values of the respective components. For example, UOS identifies an offset voltage source as a component as well as the voltage of this component. R_SV is correspondingly the identification for a resistor component which here is the substitute resistor of a lambda probe forward of a catalyzer as well as for the resistance value of this component.

Figure 1:
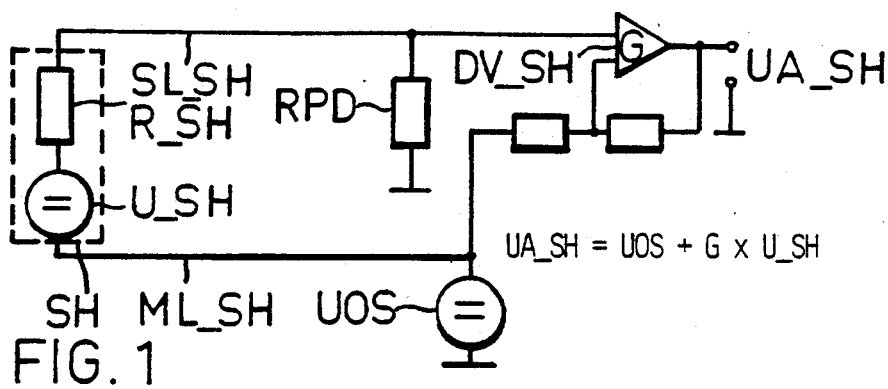
FIG. 1 is a schematic of a probe connecting circuit having an offset voltage source and a pull-down resistor.
Figure 2:
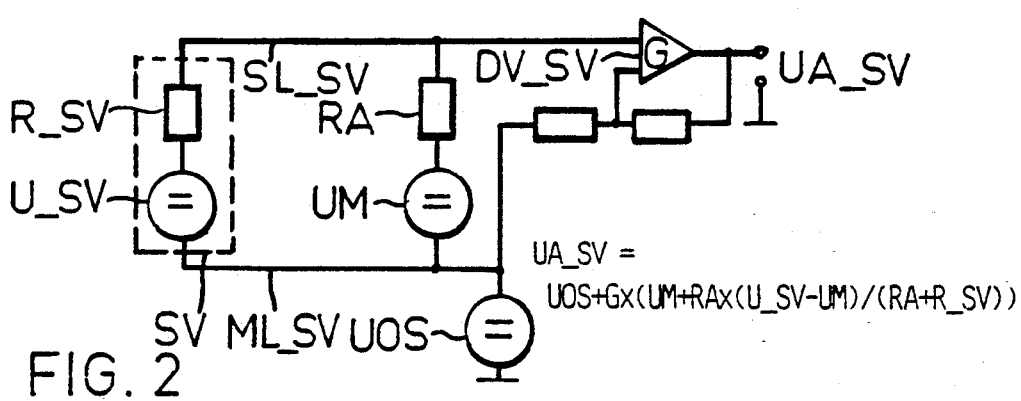
FIG. 2 is a schematic of a probe connecting circuit having an ancillary voltage source and an offset voltage source.
Figure 3:
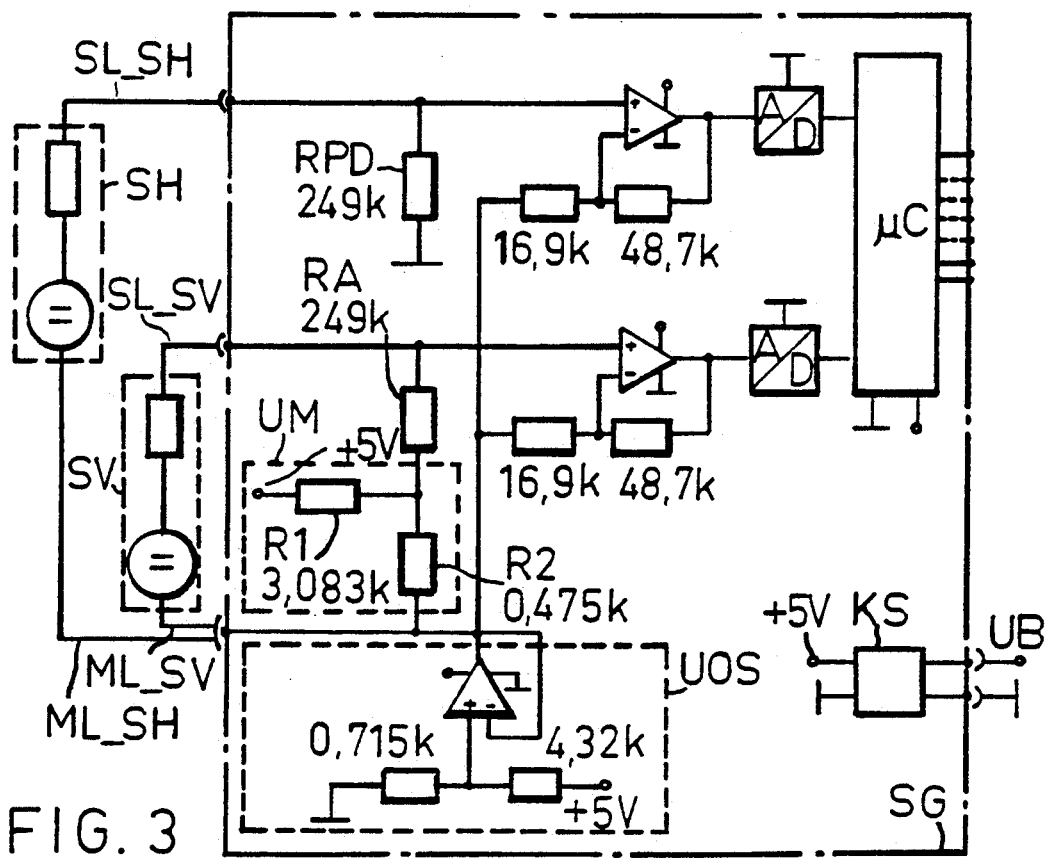
FIG. 3 is a schematic of a connecting circuit for two probes having a common offset voltage source; and, FIG. 4 is a flowchart for explaining a test method for detecting faults of a probe connecting circuit.

Before FIGS. 1 and 2 are described in detail, an introductory overview of FIG. 3 is provided.

FIG. 3 shows a control apparatus SG to which a lambda probe SV mounted forward of a catalyzer (not shown) is connected via a signal line SL_SV and a ground line ML_SV and to which a probe SH mounted rearward of the catalyzer is connected via a signal line SL_SH and a ground line ML_SH. The two ground lines lead to the same terminal of the control apparatus SG. The above-mentioned voltage source UOS is connected to this terminal within the control apparatus. With the aid of this voltage source, both ground lines are raised at high resistance to the potential UOS with respect to the control apparatus ground. The signals of both probes are supplied to a microprocessor μC. The connecting circuit for each probe includes the above-mentioned control lines up to the control apparatus SG as well as function groups in the control apparatus forward of the microprocessor.

FIG. 1 is a block diagram corresponding to the detail circuit schematic of FIG. 3 for the rearward probe SH; whereas, FIG. 2 shows the block diagram for the forward probe SV. It is here noted that this arrangement is not absolutely necessary. For example, the circuit of FIG. 1 could be used for the forward probe and the circuit of FIG. 2 for the rearward probe. However, the arrangement selected in the drawings is especially advantageous which will become apparent from the following.

In the circuit of FIG. 1, the signal line SL_SH and the ground line ML_SH of a rearward probe SH are connected to a difference amplifier DV_SH having an amplification factor G. The signal line SL_SH is connected via a pull-down resistor RPD to ground. The potential of the ground line ML_SH is raised with the aid of the above-mentioned offset voltage source UOS to the positive potential UOS with respect to ground. The output voltage UA_SH then is UOS+G×U_SH. U_SH is then the voltage supplied by the rearward probe SH. This is apparent from the equivalent circuit diagram of the probe which includes an equivalent voltage source U_SH and an equivalent probe internal resistor R_SH.

In FIG. 2, a forward probe SV is connected via the signal line SL_SV and the ground line ML_SV to a differential amplifier DV_SV. The potential of the ground line is, in turn, raised by an offset voltage source UOS to the potential UOS with respect to ground. The probe SV includes an equivalent circuit diagram having an equivalent voltage source U_SV and an equivalent resistor R_SV. The probe voltage is taken at a resistance RA which is connected in series with a voltage source UM parallel to the probe. The voltage UM generated by the voltage source UM is a mean voltage which is then supplied when the probe measures exhaust gas of a mixture having the lambda value one. The probe output voltage UA_SV is then given by:

$$US\_SV = UOS + G \times (UM + RA \times (U\_SV - UM)/(RA + R\_SV))$$

For a cold probe, the equivalent or internal resistor R_SV of the probe is very high in which case, the probe output voltage is approximately at the value UOS+G×UM.

The specific dimensioning values shown in FIG. 3 for resistances are so selected that: the difference amplifiers DV_SH and DV_SV have amplification factors G of the value 4; the voltage source UM generates a voltage of 450 mV; and, the offset voltage UOS supplied by an operational amplifier is 750 mV. In addition to the components and function groups already mentioned, the circuit of FIG. 3 includes an analog-to-digital converter between the difference amplifier DV_SH and the microcomputer μC and between the difference amplifier DV_SV and the microcomputer μC as well as a constant voltage source KS.

Figure 4:
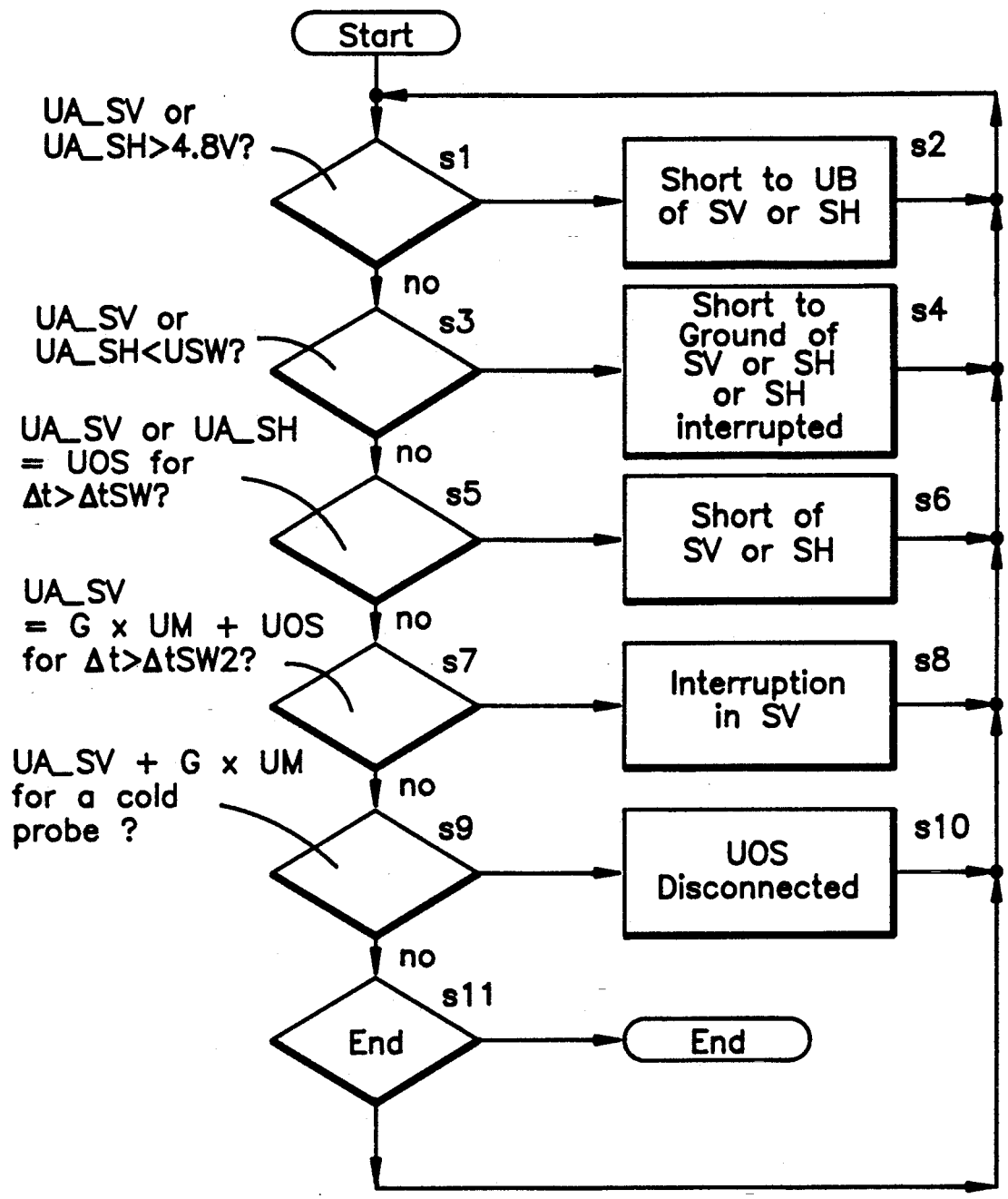

In FIG. 4, a test method is described which permits faults to be detected in the connecting circuit shown as part of FIG. 3. However, only the most important faults are discussed and especially those where the offset voltage UOS is helpful in the determination.

After the start of the method of FIG. 4, a check is first made in a step s1 as to whether one of the voltages of the two probes (that is UA_SV or UA_SH) is greater than 4.8 V. This can only be the case when a short circuit of either the signal line to the battery voltage UB or the ground line to the battery voltage UB is present. If this is actually determined, the corresponding fault announcement follows in a step s2. The fault announcement can be stored in a memory and/or the fault can be visibly and/or acoustically announced. The method then returns to the first step.

If no short circuit to the battery voltage is present, then a check is made in a step s3 as to whether one of the probe voltages UA_SV or UA_SH is less than a threshold voltage USW which is maximally the offset voltage UOS (in the embodiment 750 mV) reduced by the maximum possible amplified negative probe voltage USV or USH (in the embodiment 4×(−80 mV)). If this is the case for one of the probes, then a short circuit of this probe to ground is announced in a step s4. If the fault is determined for a probe, which is provided with a pull-down resistance in the signal line, then the nature of the fault can be an interruption of the ground line or of the signal line.

In FIGS. 1 to 3, the pull-down resistor is only shown for the circuit of the rearward probe. Such a pull-down resistor can however easily be connected to the signal line SL_SV of the forward probe SV. This affords the advantage that an interruption is determined immediately as it occurs since then the output voltage UA_SV drops below the offset voltage UOS. Without this kind of pull-down resistor, the output voltage UOS+G×UM adjusts in the circuit of FIG. 2 with the interruption of the signal line SL_SV or the ground line ML_SV. Because of the expected time-dependent trace of the signal of the probe SV described initially, it is not possible that this signal is at the above-mentioned constant value over a time span longer than several tenths of a second. In this way, the interruption fault can be determined likewise for the forward probe SV. In the case of the rearward probe, the above-mentioned value is however very plausible and, for this reason, the interruption fault for this probe can be determined only with the aid of the pull-down resistor RPD.

If the above-mentioned fault is determined in step s3, then the corresponding fault announcement takes place in step s4 and the method returns to step s1.

If steps s1 and s3 are run through without a fault announcement, a check is made in a step s5 as to whether the output voltage UA_SV or UA_SH of one of the two probes corresponds to the offset voltage UOS for a time span longer than a pregiven time span ΔtSW. The time span ΔtSW can be relatively short for checking the connecting circuit of the forward probe (in the order of magnitude of several seconds); whereas, the time span can be longer for the connecting circuit of the rearward probe, in the order of magnitude of several ten seconds. If the occurrence of the investigated condition is determined, then in step s6, a fault announcement takes place that a short circuit is present in the connecting circuit for the forward or rearward probe. Then step s1 is again reached.

If the steps s1, s3 and s5 are run through without a fault announcement, then a check is made in step s7 as to whether the output voltage UA_SV of the forward probe corresponds essentially to the value G×UM+UOS for more than a pregiven time span ΔtSW2. The time span need only be a few tenths of a second. If this condition is fulfilled, a fault announcement takes place in a step s8 that an interruption in the connecting circuit of the forward probe SV is present. Step s1 is then reached again. If no fault is detected in step s7, a check is made (step s9) as to whether for a cold probe, the output voltage UA_SV of this probe has the voltage UM of the ancillary voltage source. As described above, for high internal resistance of the probe, which is the case for cold probes, the output voltage should actually be UOS+G×UM. If in contrast, this voltage is only G×UM, this is an indication that the connection between offset voltage source UOS and the ground line is interrupted. In the advantageous circuit of the rearward probe according to FIG. 1, this fault can only be determined with difficulty without the ancillary voltage source UM. For this reason, it is advantageous to connect the ground line ML_SH for the rearward probe SH to the same terminal on the control apparatus SG to which the ground line ML_SV of the forward probe SV is connected. The interruption to the offset voltage source can then take place for both probes in common with the above-mentioned sequence of step s9. If the occurrence of the condition investigated in step s9 is determined, then the announcement follows in step s10 for the above-mentioned fault. Thereafter, step s1 follows again.

If a fault is detected, it can be advantageous not only to issue a fault announcement but also to start an emergency procedure in a known manner.

If all fault investigation steps are run through without determining a fault, then finally, in step s11, an inquiry is made if the method should be ended, for example, because the ignition has been switched off and the fault investigation cannot be carried out in an after-running phase. If it results that the method should be continued, then the inquiry begins anew starting with step s1.

All the dimensioning data relate to an engine having a two-level lambda control while using zircon-oxide probes of the Nernst type. It is for the person of experience in this area no difficulty to adapt the dimensioning to other probes and to adapt to particular dead and delay times for a specific overall configuration and to undertake a specific control since only adaptations within the same order of magnitude are required. What is essential is that the ground line is provided with a potential offset with respect to ground potential. Furthermore, it is advantageous that the signal line is provided with a pull-down resistor.

It is understood that the foregoing description is that of the preferred embodiments of the invention and that various changes and modifications may be made thereto without departing from the spirit and scope of the invention as defined in the appended claims.

What is claimed is:

1. A connecting circuit for connecting a lambda probe to a control apparatus having a control apparatus ground line, the lambda probe having a lambda probe signal line for transmitting a signal of the probe and a lambda probe ground line, the connecting circuit comprising: offset-voltage source means connected to said control apparatus ground line and said lambda probe ground line for raising the potential of said lambda probe ground line to a predetermined value relative to said control apparatus ground line.

2. The connecting circuit of claim 1, said offset-voltage source means being a high-impedance offset-voltage source means.

3. The connecting circuit of claim 1, wherein the voltage generated by said offset-voltage source means is greater than the maximum possible amplified negative voltage of said lambda probe means; and, said connecting circuit further comprising amplification means for amplifying the signal of said lambda probe on said signal line to obtain said maximum possible amplified negative voltage.

4. The connecting circuit of claim 1, further comprising a pull-down resistor connected between said signal line of said lambda probe and said control apparatus ground line.

5. The connecting circuit of claim 1, said lambda probe means comprising two lambda probes (SV, SH) having respective ground lines (ML_SV, ML_SH) connected to each other thereby causing said pregiven ground potential to be the same on both of said ground lines; and, said offset-voltage source means being connected to said ground lines for changing said pregiven ground potential on both of said ground lines to said predetermined value relative to ground.

6. A method for testing a connecting circuit for connecting a lambda probe to a control apparatus having a control apparatus ground line, the lambda probe having a lambda probe ground line and a lambda probe signal line for transmitting a signal of the lambda probe, the method comprising the steps of:

raising the potential of the ground line by a pregiven offset voltage with respect to ground potential;

amplifying the signal on said lambda probe signal line to obtain the maximum possible amplified negative probe voltage;

measuring the signal-line potential of the signal line relative to ground to determine if said signal-line potential is below a threshold value with said threshold value being at most equal to the difference between said offset voltage and the maximum possible amplified negative probe voltage; and, determining whether said signal-line potential is below said threshold value and, if so, then emitting a fault signal.

* * * * *